United States Patent [19]

Adams et al.

[11] Patent Number: 5,269,298
[45] Date of Patent: Dec. 14, 1993

[54] ATRIAL DEFIBRILLATOR AND METHOD FOR PROVIDING SYNCHRONIZED DELAYED CARDIOVERSION

[75] Inventors: John M. Adams, Issaquah; Clifton A. Alferness; Kenneth R. Infinger, both of Redmond; Yixuan Jin, Mercer Island, all of Wash.

[73] Assignee: InControl, Inc., Redmond, Wash.

[21] Appl. No.: 965,168

[22] Filed: Oct. 23, 1992

[51] Int. Cl.⁵ .............................. A61N 1/39
[52] U.S. Cl. ................................ 128/419 D
[58] Field of Search .................... 128/419 D

[56] References Cited

U.S. PATENT DOCUMENTS

| | | | |
|---|---|---|---|
| 3,236,239 | 2/1966 | Berkovits | 128/419 D |
| 3,738,370 | 6/1973 | Charms | 128/419 D |
| 3,952,750 | 4/1976 | Mirowski et al. | 128/419 D |
| 4,094,310 | 6/1978 | McEachern et al. | 128/419 D |
| 4,300,567 | 11/1981 | Kolenik et al. | 128/419 D |
| 4,384,585 | 5/1983 | Zipes | 128/419 D |
| 4,516,579 | 5/1985 | Irnich | 128/419 PG |
| 5,007,422 | 4/1991 | Pless et al. | 128/419 PG |
| 5,105,809 | 4/1992 | Bach, Jr. et al. | 128/419 D |
| 5,129,392 | 7/1992 | Bardy et al. | 128/419 D |
| 5,165,403 | 11/1992 | Mehra | 128/419 D |

Primary Examiner—William E. Kamm
Assistant Examiner—Kennedy J. Schaetzle
Attorney, Agent, or Firm—Foley & Lardner

[57] ABSTRACT

An implantable atrial defibrillator provides cardioverting electrical energy to the atria of a human heart in need of cardioversion. The atrial defibrillator includes a first detector for detecting ventricular activations of the heart, a second detector for detecting atrial activity of the heart, and an atrial fibrillation detector responsive to the second detector for determining when the atria of the heart are in need of cardioversion. The atrial defibrillator further includes a cardioverter for applying the cardioverting electrical energy to the atria of the heart when the atria of the heart are in need of cardioversion, and a timer delay stage responsive to the first detector for causing the cardioverter to apply the cardioverting electrical energy to the atria of the heart a predetermined delay time after the first detector detects one of the ventricular activations and before the T wave of the heart immediately following the one of the ventricular activations.

11 Claims, 1 Drawing Sheet

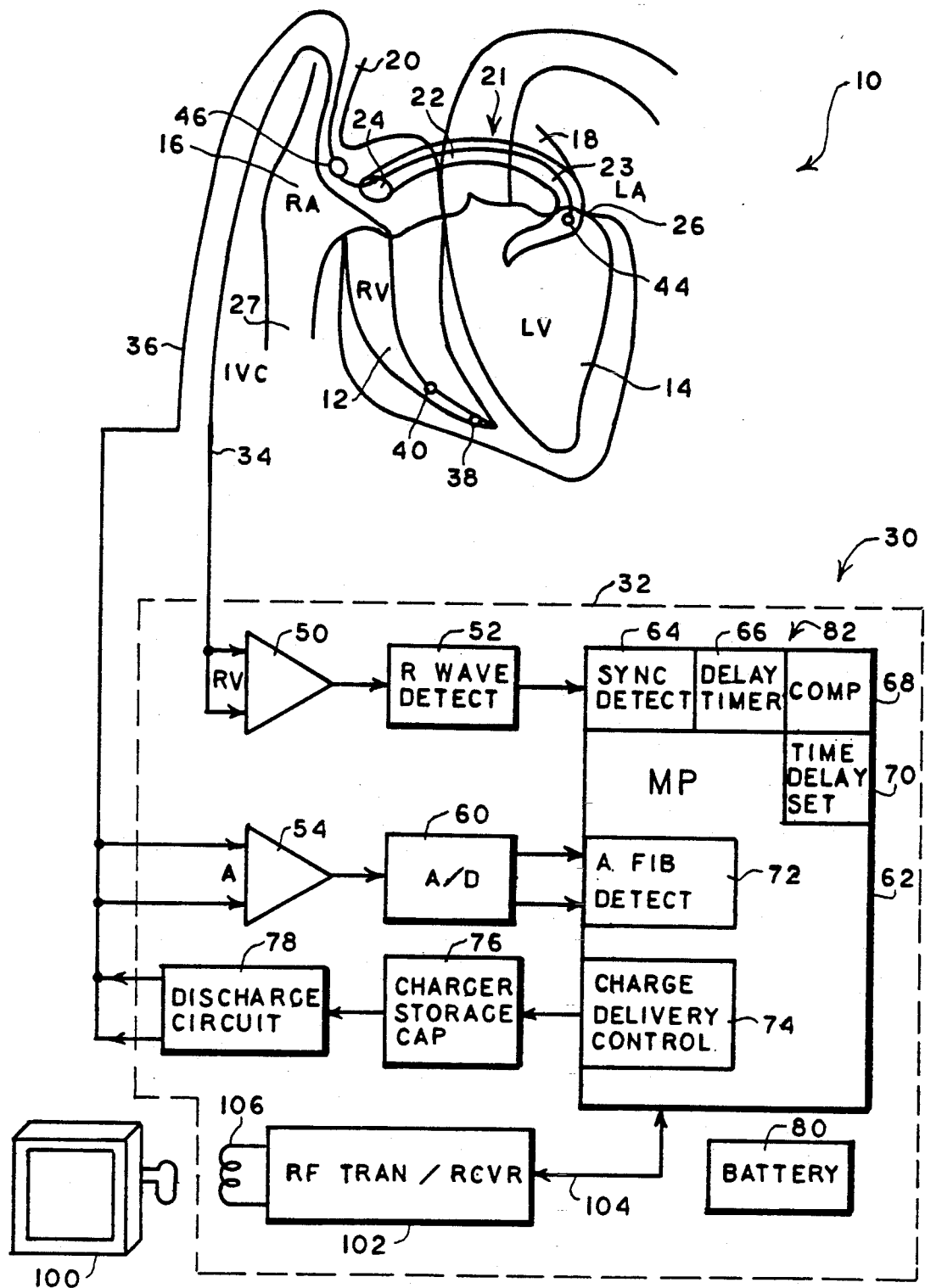

ATRIAL DEFIBRILLATOR AND METHOD FOR PROVIDING SYNCHRONIZED DELAYED CARDIOVERSION

BACKGROUND OF THE INVENTION

The present invention generally relates to an atrial defibrillator and method for applying cardioverting electrical energy to the atria of a human heart in need of cardioversion. The present invention is more particularly directed to a fully automatic implantable atrial defibrillator which exhibits improved safety by reducing the potential risk of induced ventricular fibrillation which may result from the mistimed delivery of cardioverting electrical energy to the atria. More specifically, the atrial defibrillator and method of the present invention guards against applying cardioverting electrical energy to the atria under conditions believed to contribute to induced ventricle fibrillation.

Atrial fibrillation is probably the most common cardiac arrhythmia. Although it is not usually a life threatening arrhythmia, it is associated with strokes thought to be caused by blood clots forming in areas of stagnant blood flow as a result of prolonged atrial fibrillation. In addition, patients afflicted with atrial fibrillation generally experience palpitations of the heart and may even experience dizziness or even loss of consciousness.

Atrial fibrillation occurs suddenly and many times can only be corrected by a discharge of electrical energy to the heart through the skin of the patient by way of an external defibrillator of the type well known in the art. This treatment is commonly referred to as synchronized cardioversion and, as its name implies, involves applying electrical defibrillating energy to the heart in synchronism with a detected ventricular electrical activation (R wave) of the heart. The treatment is very painful and, unfortunately, most often only results in temporary relief for patients, lasting but a few weeks.

Drugs are available for reducing the incidence of atrial fibrillation. However, these drugs have many side effects and many patients are resistent to them which greatly reduces their therapeutic effect.

Implantable atrial defibrillators have been proposed to provide patients suffering from occurrences of atrial fibrillation with relief. Unfortunately, to the detriment of such patients, none of these atrial defibrillators have become a commercial reality.

Implantable atrial defibrillators proposed in the past have exhibited a number of disadvantages which probably has precluded these defibrillators from becoming a commercial reality. Two such proposed defibrillators, although represented as being implantable, were not fully automatic, requiring human interaction for cardioverting or defibrillating the heart. Both of these proposed defibrillators require the patient to recognize the symptoms of atrial fibrillation with one defibrillator requiring a visit to a physician to activate the defibrillator and the other defibrillator requiring the patient to activate the defibrillator from external to the patient's skin with a magnet.

Improved atrial defibrillators and lead systems which exhibit both automatic operation and improved safety are fully described in copending U.S. applications, Ser. No. 07/685,130, filed Apr. 12, 1991, in the names of John M. Adams and Clifton A. Alferness for IMPROVED ATRIAL DEFIBRILLATOR AND METHOD and Ser. No. 07/856,514, filed Mar. 24, 1992, in the names of John M. Adams, Clifton A. Alferness, and Paul E. Kreyenhagen for IMPROVED ATRIAL DEFIBRILLATOR, LEAD SYSTEMS, AND METHOD, which applications are assigned to the assignee of the present invention and incorporated herein by reference. As disclosed in the aforementioned referenced applications, synchronizing the delivery of the defibrillating or cardioverting electrical energy to the atria with a ventricular electrical activation (R wave) of the heart has been considered important to avoid cardioverting the heart during the heart's vulnerable period or T wave to thus prevent induced ventricular fibrillation. Ventricular fibrillation is a fatal arrhythmia which can be caused by electrical energy being delivered to the heart at the wrong time in the cardiac cycle, such as during the T wave of the cycle. The atrial defibrillators of the aforementioned referenced applications exhibit improved safety from inducing ventricular fibrillation by sensing ventricular activations of the heart in a manner which avoids detecting noise as ventricular electrical activations for generating reliable synchronization signals. Hence, these implantable atrial defibrillators, by providing such noise immunity in R wave detection assure reliable synchronization.

Another measure for reducing the risk of inducing ventricular fibrillation during the delivery of cardioverting electrical energy to the atria of the heart employed by the defibrillators of the aforementioned referenced applications is the reduction of the amount of the electrical energy which is passed through the ventricles during cardioversion of the atria. This is achieved by locating the cardioverting electrodes in or near the heart to provide a cardioverting energy path which confines substantially all of the cardioverting electrical energy to the atria of the heart.

It has also been observed that during episodes of atrial fibrillation, the cardiac rate increases to a high rate and/or becomes extremely variable. At high cardiac rates, the R wave of each cardiac cycle becomes closely spaced from the T wave of the immediately preceding cardiac cycle. This creates a condition known in the art as an "R on T" condition which is believed to contribute to induced ventricular fibrillation if the atria are cardioverted in synchronism with the R wave close to the preceding T wave. For highly variable cardiac rates, a long cardiac cycle can be followed by a relatively short cardiac cycle. This condition is believed to cause dispersion of refractoriness and also can result in a vulnerable R on T condition. For a more complete understanding of the aforementioned highly variable cardiac rate and the consequences thereof, reference may be had to an article entitled El-Sherif et al., Reentrant Ventricular Arrhythmias in the Late Myocardial Infarction Period: Mechanisms by Which a Short-Long-Short Cardiac Sequence Facilitates the Induction of Reentry, Circulation, 83(1):268-278 (1991).

It has been further observed that as ventricular activations propagate through the heart, the right ventricle apex activates slightly prior to the superior left ventricle. Hence, if the atria are cardioverted in synchronism with an activation of the right ventricular apex, the activation of the superior left ventricle may not be completed. Recent studies have shown that cardioverting the atria when the ventricular activation is not fully completed may contribute to induced ventricular fibrillation.

The atrial defibrillator and method of the present invention greatly reduces the risk of inducing ventricular fibrillation during atrial cardioversion or defibrillation by assuring that the cardioverting electrical energy is not applied to the atria during both an R on T condition and a not yet completed ventricular activation. As will be seen hereinafter, this is accomplished by delaying the application of the cardioverting or defibrillating electrical energy until a predetermined delay time has elapsed after detecting a ventricular activation. The delay time is chosen to be of sufficient duration to assure that the ventricular activation has fully completed and of insufficient duration to avoid applying the cardioverting electrical energy to the atria during the T wave immediately following the detected ventricular activation. As a result, a reduced risk of induced ventricular fibrillation is assured because the cardioverting electrical energy will not be applied to the atria during an R on T condition, during an uncompleted ventricle activation, or during a vulnerable period of the heart.

SUMMARY OF THE INVENTION

The present invention therefore provides atrial defibrillator for providing cardioverting electrical energy to the atria of a human heart. The atrial defibrillator includes detecting means for detecting ventricular activations of the heart, cardioverting means for applying the cardioverting electrical energy to the atria of the heart, and delay means responsive to the detecting means for causing the cardioverting means to apply the cardioverting electrical energy to the atria of the heart a predetermined delay time after the first detecting means detects one of the ventricular activations and before the T wave of the heart immediately following one of the ventricular activations.

The present invention also provides an implantable atrial defibrillator for providing cardioverting electrical energy to the atria of a human heart in need of cardioversion. The atrial defibrillator includes first detecting means for detecting ventricular activations of the heart and second detecting means for detecting atrial activity of the heart. The atrial defibrillator further includes atrial defibrillation detecting means responsive to the second detecting means for determining when the atria of the heart are in need of cardioversion and cardioverting means for applying the cardioverting electrical energy to the atria of the heart when the atria of the heart are in need of cardioversion. The atrial defibrillator further includes delay means responsive to the first detecting means for causing the cardioverting means to apply the cardioverting electrical energy to the atria of the heart a predetermined delay time after the first detecting means detects on of the ventricular activations and before the T wave of the heart immediately following the one of the ventricular activations.

The present invention further provides a method of applying cardioverting electrical energy to the atria of a human heart in need of cardioversion. The method includes the steps of detecting ventricular activations of the heart, detecting atrial activity of the heart, and determining, responsive to the detected atrial activity of the heart, when the atria of the heart are in need of cardioversion. The method further includes the step of applying the cardioverting electrical energy to the atria of the heart when the atria of the heart are in need of cardioversion and a predetermined delay time after detecting one of the ventricular activations and before the T wave of the heart immediately following the one of the ventricular activations.

BRIEF DESCRIPTION OF THE DRAWINGS

The features of the present invention which are believed to be novel are set forth with particularity in the appended claims. The invention, together with further objects and advantages thereof, may best be understood by making reference to the following description taken in conjunction with the accompanying drawing, in the sole figure of which like reference numerals identify identical elements, and wherein the sole FIGURE is a schematic block diagram of a fully implantable atrial defibrillator embodying the present invention for applying defibrillating electrical energy to the atria of a human heart and which is shown in association with a human heart in need of atrial fibrillation monitoring and potential cardioversion of the atria.

DETAILED DESCRIPTION OF THE PREFERRED EMBODIMENT

Prior to referring to the sole FIGURE, a general description of a typical or normal cardiac cycle may be helpful in understanding the operation and various aspects of the present invention. The beginning of a cardiac cycle is initiated by a P wave which is normally a small positive wave. The P wave induces depolarization of the atria of the heart. Following the P wave there is a cardiac cycle portion which is substantially constant have a time duration on the order of, for example, 120 milliseconds.

The QRS complex of the cardiac cycle then normally occurs after the substantially constant portion. The dominating feature of the QRS complex is the R wave which is a rapid positive or negative deflection. The R wave generally has an amplitude greater than any other wave of the cardiac cycle and will have a spiked shape of relatively short duration with a sharp rise, a peak o amplitude, and a sharp decline. The R wave is the depolarization of the ventricles and hence, as used herein, the term "ventricle activations" denotes R waves of the heart cardiac cycle. As previously mentioned, as ventricular activations propagate through the heart, the right ventricle apex is generally depolarized slightly prior to the depolarization of the superior left ventricle.

Following the QRS complex, the cardiac cycle is completed with the T wave which is separated from the QRS complex by about 250 milliseconds. The T wave is relatively long in duration of, for example, on the order of 150 milliseconds. It is during the T wave that the heart is most vulnerable t induced ventricular fibrillation should the heart be cardioverted during this period. The next cardiac cycle begins with the next P wave. The duration of a cardiac cycle may be on the order of 800 milliseconds.

As will be appreciated by those skilled in the art, the characteristics of a cardiac cycle of a heart experiencing atrial fibrillation will be distinctly different than described above for a normal cardiac cycle. During atrial fibrillation, there generally are no discernable P waves because the atria are in an unstable or fibrillating condition. Also, the cardiac rate may be extremely high and highly variable which results in the previously referred to R on T condition where the ventricular activation (R wave) of one cardiac cycle is closely adjacent in time to the T wave of the immediately preceding cardiac cycle.

Referring now to the sole FIGURE, it illustrates a fully implantable atrial defibrillator 30 embodying the present invention shown in association with a schematically illustrated human heart 10 in need of atrial fibrillation monitoring and potential cardioversion of the atria. The portions of the heart 10 illustrated in FIG. 1 are the right ventricle 12, the left ventricle 14, the right atrium 16, the left atrium 18, the superior vena cava 20, the coronary sinus channel 21 which, as used herein, denotes the coronary sinus 22 and the great cardiac vein 23, the coronary sinus ostium or opening 24, the left ventricular free wall 26 and the inferior vena cava 27.

The atrial defibrillator 30 generally includes an enclosure 32 for hermetically sealing the internal circuit elements of the atrial defibrillator to be described hereinafter, an endocardial first lead 34, and an intravascular second lead 36. The enclosure 32 and first and second leads 34 and 36 are arranged to be implanted beneath the skin of a patient so as to render the atrial defibrillator 30 fully implantable.

The endocardial first lead 34 preferably comprises a endocardial bi-polar lead having electrodes 38 and 40 arranged for establishing electrical contact with the right ventricle 12 of the heart The electrodes 38 and 40 permit bi-polar sensing of ventricular activations in the right ventricle. As illustrated, the lead 34 is fed through the superior vena cava 20, into the right atrium 16, and then into the right ventricle 12.

The second lead 36 generally includes a first or tip electrode 44 and a second or proximal electrode 46. As illustrated, the second lead 36 is flexible and arranged to be passed down the superior vena cava 20, into the right atrium 16, into the coronary sinus ostium 24, and advanced into the coronary sinus channel 21 of the heart near the left side thereof so that the first or tip electrode 44 is within the coronary sinus channel 21 either within the coronary sinus 22 adjacent the left ventricle 14 and beneath the left atrium 18 or most preferably within the great cardiac vein 23 adjacent the left ventricle 14 and beneath the left atrium 18. The electrodes 44 and 46 are spaced apart such that when the first electrode 44 is positioned as described above, the second electrode 46 is in the right atrium 16. The first electrode 44 together with the second electrode 46 provide bi-polar sensing of heart activity in the atria 16 and 18. The first electrode 44 and the second electrode 46 further provide for the delivery o defibrillating electrical energy to the atria. Because the first electrode 44 is located beneath the left atrium 18 near the left ventricle 14 and the second electrode 46 is within the right atrium 16, the electrical energy applied between these electrodes will be substantially confined to the atria 16 and 18 of the heart 10. As a result, the electrical energy applied to the right ventricle 12 and left ventricle 14 when the atria are cardioverted or defibrillated will be minimized. This greatly reduces the potential for ventricular fibrillation of the heart to be induced as a result of the application of defibrillating electrical energy of the atria of the heart.

Within the enclosure 32, the atrial defibrillator 30 includes a first sense amplifier 50, an R wave detector 52, and a second sense amplifier 54. The first sense amplifier 50 and the R wave detector 52 form a first detecting means which together with electrodes 38 and 40 of the first lead 34 to which sense amplifier 50 is coupled, senses ventricular activations of the right ventricle 12. The second sense amplifier 54 forms a second detecting means which, together with the first electrode 44 and second electrode 46 of the second lead 36 to which it is coupled detects atrial activity of the heart.

The output of the first sense amplifier 50 is coupled to the R wave detector 52. The R wave detector 52 is of the type well known in the art which provides an output pulse upon the occurrence of an R wave being sensed during a cardiac cycle of the heart. The output of the second sense amplifier 54 is coupled to an analog to digital converter 60 which converts the analog signal representative of the atrial activity of the heart being detected to digital samples for further processing in a manner to be described hereinafter.

The enclosure 32 of the atrial defibrillator 30 further includes a microprocessor 62. The microprocessor 62 is preferably implemented in a manner as disclosed in the aforementioned copending U.S. applications, Ser. Nos. 07/685,130 and 07/856,514 and further as described hereinafter. The implementation of the microprocessor 62 in accordance with this embodiment of the present invention results in a plurality of functional stages. The stages include a synchronization detector 64, a delay timer stage 66, a comparator stage 68, a time delay set stage 70, an atrial arrhythmia detector in the form of an atrial fibrillation detector 72, and a charge delivery and energy control stage 74.

The microprocessor 62 is arranged to operate in conjunction with a memory (not shown) which may be coupled to the microprocessor 62 by a multiple-bit address bus (not shown) and a bi-directional multiple-bit databus (not shown). This permits the microprocessor 62 to address desired memory locations within the memory for executing write or read operations. During a write operation, the microprocessor stores data, such as time intervals or operating parameters in the memory at the addresses defined by multiple-bit addresses conveyed over the address bus and coveys the data to the memory 92 over the multiple-bit data bus. During a read operation, the microprocessor 62 obtains data from the memory at the storage locations identified by the multiple-bit addresses provided over the address bus and receives the data from the memory over the bi-directional data bus.

For entering operating parameters into the microprocessor 62, as for example the time delay referred to hereinafter into time delay set stage 70, the microprocessor 62 receives programmable operating parameters from an external controller 100 which is external to the skin of the patient. The external controller 100 is arranged to communicate with a receiver/transmitter 102 within enclosure 32 which is coupled to the microprocessor 62 over a bi-directional bus 104. The receiver/transmitter 102 may be of the type well known in the art for conveying various information which it obtains from the microprocessor 62 to the external controller 100 or for receiving programming parameters from the external controller 100 which the receiver/transmitter 102 then conveys to the microprocessor 62 for storage in internal memory, such as in time delay set stage 70, or in the aforementioned external memory within enclosure 32.

The receiver/transmitter 102 includes a transmitting coil 106 so that the receiver/transmitter 102 and coil 106 form a communication means. Such communication means are well known in the art and may be utilized as noted above for receiving commands from external to the implantable enclosure 32 and for transmitting data to the external controller 100 from the implanted enclosure 32. One such communication system is disclosed, for example, in U.S. Pat. No. 4,586,508.

To complete the identification of the various structural elements within the enclosure 32, the atrial defibrillator 30 further includes a charger and storage capacitor circuit 76 of the type well known in the art which charges a storage capacitor to a predetermined voltage level and a discharge circuit 78 for discharging the storage capacitor within circuit 76 by a predetermined amount to provide a controlled discharge output of electrical energy when required to the atria of the heart. To that end, the discharge circuit 78 is coupled to the first electrode 44 and the second electrode 46 of the second lead 36 for applying the cardioverting or defibrillating electrical energy to the atria. Lastly, the defibrillator 30 includes a depletable power source 80, such a lithium battery, for providing power to the electrical components of the atrial defibrillator 30.

The sense amplifier 50 and the R wave detector 52 continuously detect the occurrence of ventricular activations of the right ventricle 12. As disclosed in the aforementioned copending U.S. applications Ser. Nos. 07/685,130 and 07/856,514, herein incorporated by reference, when the time intervals between immediately successive R waves indicate the probability of an episode of atrial fibrillation, the microprocessor 62 enables the atrial fibrillation detector 72, sense amplifier 54, and the analog to digital converter 60. If the atrial fibrillation detector 72 determines that the atria 16 and 18 are in fibrillation and thus in need of cardioversion, the charge delivery control 74 causes the charger and storage capacitor circuit 76 to charge the storage capacitor within circuit 76. The atrial defibrillator 30 is then ready to apply cardioverting electrical energy to the atria 16 and 18 at the appropriate time in a manner described hereinafter.

The synchronization detector 64, the delay timer 66, the comparator 68, and the time delay set stage 70 form a delay means 82 for delaying the application of the cardioverting electrical energy to the atria 16 and 18 of the heart 10 until after a predetermined delay time following the detection of a ventricular activation by the sense amplifier 50 and the R wave detector 52. The predetermined delay time is previously entered into the time delay set stage 70 from the external controller 100 and through the transmitter/receiver 102 as previously described. Also, the delay timer is reset when the storage capacitor in circuit 76 reaches full charge.

The synchronization detector 64 provides a pulse to the delay timer in response to the pulse from the R wave detector upon the detection of a ventricular activation. Prior to starting the delay timer however, and in accordance with the aforementioned cross referenced copending applications, Ser. Nos. 07/685,130 and 07/856,514, synchronization pulse counting may be employed wherein the synchronization detector 64 first counts a predetermined number, such as five, consecutive R wave detect pulses from R wave detector 52 to assure that there is still reliable detection of the ventricular activations.

Upon the sixth pulse from R wave detector 52 (if such pulse counting is employed) or upon the first pulse from R wave detector 52 (if such pulse counting is not employed), the synchronization counter 64 provides its pulse to delay timer 66 to start the delay timer. The comparator 68 then continuously compares the time kept by the delay timer 66 to the predetermined delay time stored in the time delay set stage 70. When the time kept by the delay timer 66 equals the stored delay time, the comparator 68 causes the charge delivery control 74 to provide a control signal to the discharge circuit 78 for discharging the cardioverting electrical energy stored in circuit 76 between electrodes 46 and 44. This applies the cardioverting electrical energy to the atria 16 and 18 of the heart.

As a result of the foregoing, the cardioverting electrical energy is applied to the atria when the atria are in need of cardioversion and a predetermined delay time after one of the ventricular activations is detected. The delay time is selected to be long enough to assure that the ventricular activation, which ultimately starts delay timer 66, is completed and short enough so as to avoid cardioverting the atria during the T wave which immediately follows the ventricular activation in about 250 milliseconds. As an example, and without limitations, the delay time may be in the range of five to eighty milliseconds. The range of suitable delay times, of course, will depend upon the particular heart physiology of a particular patient.

In controlling the application or delivery of the cardioverting electrical energy in the foregoing manner, it will be assured that the atria are not cardioverted during a partially completed ventricular activation, an R on T condition, or the vulnerable period T wave of the heart. The present invention hence provides an improved atrial defibrillator and method which exhibits increased safety in reducing the risk of inducing ventricular fibrillation when cardioverting the atria of the heart.

While a particular embodiment of the present invention has been shown and described, modifications may be made. For example, the delayed cardioversion of the present invention may be utilized to advantage in an external atrial defibrillator wherein an electrode or electrodes adhered to the surface of the skin of a patient are employed along with an R wave detector for detecting ventricular activations and surface pad electrodes are utilized for applying the cardioverting electrical energy to the atria of the heart. Such surface detecting and pad electrodes are well known in the art. Hence, it is therefore intended in the appended claims to cover all such changes and modifications which fall within the true spirit and scope of the invention.

What is claimed is:

1. An implantable atrial defibrillator for providing cardioverting electrical energy to the atria of a human heart in need of cardioversion, said atrial defibrillator comprising:

first detecting means for detecting ventricular activations of the heart;

second detecting means for detecting atrial activity of the heart;

atrial fibrillation detecting means responsive to said second detecting means for determining when the atria of the heart are in need of cardioversion;

cardioverting means for applying said cardioverting electrical energy to the atria of the heart when the atria of the heart are in need of cardioversion; and delay means responsive to said first detecting means for causing said cardioverting means to apply said cardioverting electrical energy to the atria of the heart a predetermined delay time after said first detecting means detects one of said ventricular activations and before the T wave of the heart immediately following said one of said ventricular activations.

2. An atrial defibrillator as defined in claim 1 wherein said predetermined delay time is of sufficient duration for the completion of said one of said ventricular activations.

3. An atrial defibrillator as defined in claim 1 wherein said predetermined delay time is between five and eighty milliseconds.

4. An atrial defibrillator as defined in claim 1 wherein said delay means includes timing means responsive to said first detecting means for timing said predetermined delay time.

5. An atrial defibrillator as defined in claim 4 wherein said delay means further includes a synchronizing detector for starting said timing means responsive to said first detecting means detecting said one of said ventricular activations.

6. An atrial defibrillator as defined in claim 5 wherein said delay means further includes comparing means for comparing the time of said timing means to said predetermined delay time and for causing said cardioverting mean to apply said cardioverting electrical energy to the atria of the heart when the time of said timing means equals said predetermined delay time.

7. A method of applying cardioverting electrical energy to the atria of a human heart in need of cardioversion, said method including the steps of:
   detecting ventricular activations of the heart;
   detecting atrial activity of the heart;
   determining, responsive to said detected atrial activity of the heart, when the atria of the heart are in need of cardioversion; and
   applying said cardioverting electrical energy to the atria of the heart when the atria of the heart are in need of cardioversion and a predetermined delay time after detecting one of said ventricular activations and before the T wave of the heart immediately following said one of said ventricle activations.

8. A method as defined in claim 7 wherein said predetermined delay time is of sufficient duration for the completion of said one of said ventricular activations.

9. A method as defined in claim 7 wherein said predetermined delay time is between five and eighty milliseconds.

10. A method as defined in claim 1 including the further step of timing said predetermined delay time upon detecting said one of said ventricular activations.

11. An atrial defibrillator for providing cardioverting electrical energy to the atria of a human heart, said atrial defibrillator comprising:
   detecting means for detecting ventricular activations of the heart;
   cardioverting means for applying said cardioverting electrical energy to the atria of the heart; and
   delay means responsive to said detecting means for causing said cardioverting means to apply said cardioverting electrical energy to the atria of the heart a predetermined delay time after said detecting means detects one of said ventricular activations and before the T wave of the heart immediately following said one of said ventricular activations.

* * * * *